US011896602B2

(12) United States Patent
Jost et al.

(10) Patent No.: US 11,896,602 B2
(45) Date of Patent: *Feb. 13, 2024

(54) METHOD FOR PREVENTING PREGNANCY

(71) Applicant: ESTETRA SRL, Liège (BE)

(72) Inventors: Maud Jost, Liège (BE); Glwadys Rausin, Liège (BE)

(73) Assignee: ESTETRA SRL, Liege (BE)

( * ) Notice: Subject to any disclaimer, the term of this patent is extended or adjusted under 35 U.S.C. 154(b) by 0 days.

This patent is subject to a terminal disclaimer.

(21) Appl. No.: 17/937,215

(22) Filed: Sep. 30, 2022

(65) Prior Publication Data

US 2023/0041304 A1  Feb. 9, 2023

Related U.S. Application Data

(63) Continuation of application No. 16/323,110, filed as application No. PCT/EP2017/069908 on Aug. 7, 2017.

(30) Foreign Application Priority Data

Aug. 5, 2016 (EP) ..................................... 16183025
Oct. 28, 2016 (WO) ................. PCT/EP2016/076104

(51) Int. Cl.
A61K 31/585 (2006.01)
A61K 31/565 (2006.01)
A61P 15/00 (2006.01)
A61K 31/566 (2006.01)

(52) U.S. Cl.
CPC .......... *A61K 31/585* (2013.01); *A61K 31/565* (2013.01); *A61K 31/566* (2013.01); *A61P 15/00* (2018.01)

(58) Field of Classification Search
CPC .............. A61K 2300/00; A61K 31/565; A61K 31/566; A61K 31/585; A61P 15/00
See application file for complete search history.

(56) References Cited

U.S. PATENT DOCUMENTS

| 3,138,588 | A | 6/1964 | Smith |
| 3,433,785 | A | 3/1969 | PPhillips et al. |
| 5,073,374 | A | 12/1991 | McCarty |
| 5,340,586 | A | 8/1994 | Pike et al. |
| 6,117,446 | A | 9/2000 | Place |
| 6,475,510 | B1 | 11/2002 | Venkatesh et al. |
| 6,723,348 | B2 | 4/2004 | Faham et al. |
| 7,723,320 | B2 | 5/2010 | Bunschoten et al. |
| 7,732,430 | B2 | 6/2010 | Bunschoten et al. |
| 7,871,995 | B2 | 1/2011 | Bunschoten et al. |
| 7,923,440 | B2 | 4/2011 | Bunschoten et al. |
| 7,943,604 | B2 | 5/2011 | Coelingh Bennink et al. |
| 8,026,228 | B2 | 9/2011 | Coelingh Bennink et al. |
| 8,048,869 | B2 | 11/2011 | Bunschoten et al. |
| 8,236,785 | B2 | 8/2012 | Coelingh Bennink |
| 8,303,868 | B2 | 11/2012 | Maruyama |
| 8,367,647 | B2 | 2/2013 | Coelingh Bennink et al. |
| 8,518,923 | B2 | 8/2013 | Visser et al. |
| 8,808,735 | B2 | 8/2014 | Bertelsen et al. |
| 8,987,240 | B2 | 3/2015 | Coelingh Bennink et al. |
| 8,987,484 | B2 | 3/2015 | Pascal |
| 9,034,854 | B2 | 5/2015 | Coelingh Bennink et al. |
| 9,040,509 | B2 | 5/2015 | Coelingh Bennink et al. |
| 9,238,035 | B2 | 1/2016 | Foidart et al. |
| 9,561,238 | B2 | 2/2017 | Coelingh Bennink et al. |
| 9,579,329 | B2 | 2/2017 | Wouters et al. |
| 9,603,860 | B2 | 3/2017 | Perrin et al. |
| 9,884,064 | B2 | 2/2018 | Platteeuw et al. |
| 9,987,287 | B2 | 6/2018 | Platteeuw et al. |
| 9,988,417 | B2 | 6/2018 | Ferreiro Gil et al. |
| 10,000,524 | B2 | 6/2018 | Verhaar et al. |
| 10,179,140 | B2 | 1/2019 | Perrin et al. |
| 10,201,611 | B2 | 2/2019 | Bennink et al. |
| 10,660,903 | B2 | 5/2020 | Jaspart et al. |
| 10,888,518 | B2 | 1/2021 | Jaspart et al. |
| 10,894,014 | B2 | 1/2021 | Jaspart et al. |
| 11,147,771 | B2 | 10/2021 | Jaspart et al. |
| 11,452,733 | B2 | 9/2022 | Taziaux et al. |

(Continued)

FOREIGN PATENT DOCUMENTS

| CA | 2819663 | 7/2012 |
| CL | 200501207 | 5/2005 |

(Continued)

OTHER PUBLICATIONS

Clinical Trials (E4Relief (Response to Estetrol in Life Improvement for MEnopausal-associated Hot Flushes), *E4Relief (Response to Estetrol in Life Improvement for MEnopausal-associated Hot Flushes)—Full Text View—ClinicalTrials.gov.pdf , Jul. 15, 2016).*
Odlind et al., "Can changes in sex hormone binding globulin predict the risk of venous thromboembolism with combined oral contraceptive pills?", Acta Obstet. Gynecol. Scand., 81 (6), p. 482-490.
Office Action (Advisory Action) dated Apr. 13, 2018 in U.S. Appl. No. 15/185,337 (US 2016-0367567).
Office Action dated Jan. 3, 2018 in U.S. Appl. No. 15/185,337 (US 2016-0367567 A1).
Office Action dated Jul. 3, 2017 in U.S. Appl. No. 15/185,337 (US 2016-0367567 A1).
Office Action dated Mar. 28, 2019 in U.S. Appl. No. 16/025,719 (US 2019-015759).
Office Action dated Apr. 16, 2020, in U.S. Appl. No. 16/323,110 (US 2019-0167700).
Office Action dated Apr. 23, 2021, in U.S. Appl. No. 16/323,110 (US 2019-0167700).

(Continued)

*Primary Examiner* — Savitha M Rao
(74) *Attorney, Agent, or Firm* — Foley & Lardner LLP

(57) ABSTRACT

The present invention relates to a method for the management of dysmenorrhea involving administration of an estrogenic component which is preferably selected from the group consisting of estetrol and estetrol-like compounds. Estetrol-like compounds have been surprisingly found to be capable of mitigating dysmenorrhea, either when used alone or in combination with progestogenic components, and this to an extent surpassing the effect obtained with other compositions and with a favourable side-effect profile compared to currently available methods.

20 Claims, No Drawings

(56) References Cited

U.S. PATENT DOCUMENTS

| | | |
|---|---|---|
| 11,484,539 B2 | 11/2022 | Taziaux et al. |
| 11,666,585 B2 | 6/2023 | Taziaux et al. |
| 2002/0132801 A1 | 9/2002 | Heil et al. |
| 2002/0193356 A1 | 12/2002 | Van Beek et al. |
| 2004/0009960 A1 | 1/2004 | Heil et al. |
| 2004/0192620 A1 | 9/2004 | Bunschoten et al. |
| 2004/0198671 A1 | 10/2004 | Bunschoten et al. |
| 2005/0032755 A1 | 2/2005 | Van Look et al. |
| 2005/0070488 A1 | 3/2005 | Coelingh Bennik et al. |
| 2005/0113350 A1 | 5/2005 | Duesterberg et al. |
| 2005/0147670 A1 | 7/2005 | Hsu et al. |
| 2005/0261209 A1 | 11/2005 | Bunschoten et al. |
| 2006/0063723 A1 | 3/2006 | Coelingh Bennink et al. |
| 2006/0211669 A1 | 9/2006 | Verhaar et al. |
| 2006/0276414 A1 | 12/2006 | Coelingh Bennink et al. |
| 2007/0048369 A1 | 3/2007 | Foreman et al. |
| 2007/0286819 A1 | 12/2007 | DeVries et al. |
| 2008/0113953 A1 | 5/2008 | De Vries et al. |
| 2008/0234240 A1* | 9/2008 | Dusterberg .......... A61K 31/569 514/170 |
| 2010/0093679 A1 | 4/2010 | Heil et al. |
| 2011/0021504 A1 | 1/2011 | Andreella et al. |
| 2011/0250274 A1 | 10/2011 | Shaked et al. |
| 2012/0128733 A1 | 5/2012 | Perrin et al. |
| 2012/0220556 A1 | 8/2012 | Heil et al. |
| 2014/0107091 A1 | 4/2014 | Pascal |
| 2014/0107358 A1 | 4/2014 | Pascal |
| 2014/0235882 A1 | 8/2014 | Platteeuw et al. |
| 2015/0045300 A1 | 2/2015 | Ahuja et al. |
| 2015/0098978 A1 | 4/2015 | Gao et al. |
| 2015/0133413 A1 | 5/2015 | Bennink et al. |
| 2015/0182540 A1 | 7/2015 | Heil et al. |
| 2016/0101116 A1 | 4/2016 | Foidart et al. |
| 2016/0310506 A1 | 10/2016 | Platteeuw et al. |
| 2016/0367567 A1 | 12/2016 | Jaspart et al. |
| 2017/0196886 A1 | 7/2017 | Wouters et al. |
| 2017/0216318 A1 | 8/2017 | Perrin et al. |
| 2017/0369521 A1 | 12/2017 | Platteeuw et al. |
| 2018/0153801 A1 | 6/2018 | Jaspart et al. |
| 2018/0169022 A1 | 6/2018 | Jaspart et al. |
| 2018/0185271 A1 | 7/2018 | Jaspart et al. |
| 2018/0265540 A1 | 9/2018 | Verhaar et al. |
| 2019/0125759 A1 | 5/2019 | Jaspart et al. |
| 2019/0167700 A1 | 6/2019 | Jost et al. |
| 2020/0046729 A1 | 2/2020 | Jost et al. |
| 2020/0352959 A1 | 11/2020 | Jaspart et al. |
| 2021/0154211 A1 | 5/2021 | Taziaux et al. |
| 2021/0154212 A1 | 5/2021 | Taziaux et al. |
| 2022/0096385 A1 | 3/2022 | Jaspart et al. |
| 2022/0211722 A1 | 7/2022 | Foidart |
| 2023/0025785 A1 | 1/2023 | Taziaux et al. |
| 2023/0031329 A1 | 2/2023 | Taziaux et al. |
| 2023/0073911 A1 | 3/2023 | Taziaux et al. |

FOREIGN PATENT DOCUMENTS

| | | |
|---|---|---|
| CL | 201400802 | 4/2014 |
| CL | 2013003435 A1 | 8/2014 |
| CN | 1197387 A | 10/1998 |
| CN | 1482921 | 3/2004 |
| CN | 101378762 A | 3/2009 |
| CN | 101443015 A | 5/2009 |
| CN | 101541326 A | 9/2009 |
| CN | 101631536 A | 1/2010 |
| CN | 107787224 | 3/2018 |
| CN | 102058604 A | 5/2018 |
| EP | 0 136 011 A2 | 4/1985 |
| EP | 0 286 581 A1 | 10/1988 |
| EP | 0 371 466 A1 | 6/1990 |
| EP | 0 646 592 A | 4/1995 |
| EP | 2 001 0201.7 | 11/2002 |
| EP | 0 748 190 B1 | 7/2003 |
| EP | 1 700 602 A1 | 9/2006 |
| EP | 3 046 928 B1 | 7/2016 |
| EP | 3 106 148 A1 | 12/2016 |
| JP | H03-237557 | 10/1991 |
| JP | 2005-523283 T | 8/2004 |
| JP | 2015-514731 T | 5/2015 |
| JP | 2010-513514 T | 10/2018 |
| JP | 2018-165263 A | 10/2018 |
| WO | WO-95/17895 | 7/1995 |
| WO | WO-96/03929 A1 | 2/1996 |
| WO | WO-00/42955 A1 | 7/2000 |
| WO | WO-01/05806 A1 | 1/2001 |
| WO | WO-01/40255 A2 | 6/2001 |
| WO | WO-01/52857 | 7/2001 |
| WO | WO-02/49675 A1 | 6/2002 |
| WO | WO-02/094275 A1 | 11/2002 |
| WO | WO-02/094276 A1 | 11/2002 |
| WO | WO-02/094278 A1 | 11/2002 |
| WO | WO-02/094279 A1 | 11/2002 |
| WO | WO-03/041718 A1 | 5/2003 |
| WO | WO-2004/000197 | 12/2003 |
| WO | WO-2004/006936 A1 | 1/2004 |
| WO | WO-2004/019954 A1 | 3/2004 |
| WO | WO-2004/041289 A1 | 5/2004 |
| WO | WO-2004/103377 A1 | 12/2004 |
| WO | WO-2005/030175 A1 | 4/2005 |
| WO | WO-2005/030176 A1 | 4/2005 |
| WO | WO-2005/051400 A1 | 6/2005 |
| WO | WO-2005/105103 A2 | 11/2005 |
| WO | WO-2005/115349 A1 | 12/2005 |
| WO | WO-2005/115351 A1 | 12/2005 |
| WO | WO-03/018026 A1 | 3/2006 |
| WO | WO-2006/027347 A1 | 3/2006 |
| WO | WO-2006/120035 A2 | 11/2006 |
| WO | WO-2006/125800 A2 | 11/2006 |
| WO | WO-2007/002823 | 1/2007 |
| WO | WO-2007/081206 A1 | 7/2007 |
| WO | WO-2007/106264 A2 | 9/2007 |
| WO | WO-2007/146805 | 12/2007 |
| WO | WO-2008/003363 A1 | 1/2008 |
| WO | WO-2008/003432 A1 | 1/2008 |
| WO | WO-2008/156365 A1 | 12/2008 |
| WO | WO-2010/033832 A2 | 3/2010 |
| WO | WO-2010/089078 A1 | 8/2010 |
| WO | WO-2010/149273 A1 | 12/2010 |
| WO | WO-2011/128336 A1 | 10/2011 |
| WO | WO-2011/128338 | 10/2011 |
| WO | WO-2012/000981 A1 | 1/2012 |
| WO | WO-2012/055840 A1 | 5/2012 |
| WO | WO-2013/012326 A1 | 1/2013 |
| WO | WO-2013/021025 A1 | 2/2013 |
| WO | WO-2013/090117 A1 | 6/2013 |
| WO | WO-2014/159377 A1 | 10/2014 |
| WO | WO-2014/189836 A1 | 11/2014 |
| WO | WO-2014/189838 | 11/2014 |
| WO | WO-2015/040051 A1 | 3/2015 |
| WO | WO-2015/086643 A1 | 6/2015 |
| WO | WO-2016/053946 A1 | 4/2016 |
| WO | WO-2016/187269 A1 | 11/2016 |
| WO | WO-2016/023009 A1 | 12/2016 |
| WO | WO-2016/203006 A1 | 12/2016 |
| WO | WO-2016/203009 A1 | 12/2016 |
| WO | WO-2016/207298 A1 | 12/2016 |
| WO | WP-2016/203011 A1 | 12/2016 |
| WO | WP-2016/203044 A1 | 12/2016 |
| WO | WO-2018/024912 A1 | 2/2018 |
| WO | WO-2018/065076 A | 4/2018 |
| WO | WO-2019/154899 A1 | 8/2019 |
| WO | WO-2019/202141 A1 | 10/2019 |
| WO | WO-2019/202142 A1 | 10/2019 |
| WO | WO-2021/209591 | 10/2021 |

OTHER PUBLICATIONS

Office Action dated Dec. 15, 2021, in Dominican patent application No. P2019-0108.

Office Action dated Dec. 2, 2019 in U.S. Appl. No. 15/737,189 (US 2018-0153801).

Office Action dated Dec. 6, 2019, in U.S. Appl. No. 16/573,611 (US 2020-0046729).

(56) References Cited

OTHER PUBLICATIONS

Office Action dated Feb. 3, 2020, in U.S. Appl. No. 16/573,611 (US 2020-0046729).
Office Action dated Feb. 6, 2020, in U.S. Appl. No. 15/737,227 (US 2018-0169022).
Office Action dated Jan. 18, 2022, in U.S. Appl. No. 16/323,110 (US 2019-0167700).
Office Action dated Jul. 2, 2020 in U.S. Appl. No. 16/573,611 (US 2020-0046729).
Office Action dated Jun. 27, 2019 in U.S. Appl. No. 15/737,227 (US 2018-0169022).
Office Action dated Mar. 19, 2020, in Chilean Application No. 201901152.
Office Action dated Mar. 28, 2019, in U.S. Appl. No. 16/025,719 (US 2019-0125759).
Decision of Reexamination dated Jan. 12, 2022 ("Office Action") in the Chinese patent application No. Chinese patent application No. 201680035626.3.
Guo Huiling, Pharmaceutics, editor in Chief: Guo Huiling, et al., pp. 334-335, Sun Yat-sen University Press, published on Feb. 28, 2014.
Kluft et al., "Oral contraceptive formulations with estetrol as an estrogen, in combination with levonorgestrel or drospirenone, show minor effects on haemostasis." Journal of Thrombosis and Haemostasis, Jul. 4, 2013, vol. 11, No. s2, pp. 737.
Matsumoto Mitsuo et al. Pharmaceutics Manual, Nanzando Co., Ltd., 1989, p. 83.
NCT02834312, "E4Relief (Response to Estetrol in Life Improvement for Menopausal-associated Hot Flushes)," ClinicalTrials.Gov (Jul. 12, 2016).
NCT02834312, "E4Relief (Response to Estetrol in Life Improvement for Menopausal-associated Hot Flushes)," ClinicalTrials.Gov (Jul. 28, 2016).
Office Action dated Jan. 4, 2022 in the Japanese divisional patent application No. 2021-022465.
Office Action dated Sep. 21, 2020 in the Chinese patent application No. 201680035626.3.
Royal Hanson et al "Handbook of Dissolution Testing" 3rd edition,, translated by Ning Baoming, p. 66, China Medical Science Press.
Thurston et al., Obstet Gynecol Clin North Am. Sep. 2011 ; 38(3): 489-501 (Year: 2011).
Apter, D. et al., "Estetrol combined with drospirenone: an oral contraceptive with high acceptability, user satisfaction, well-being and favourable body weight control", The European Journal of Contraception and Reproductive Health Care, vol. No. 22, Issue No. 4, 2017, pp. 260-267.
Archer et al., "A randomized, double-blind, placebo-controlled study of the lowest effective dose of drospirenone with 17β-estradiol for moderate to severe vasomotor symptoms in postmenopausal women," (2014) Menopause, vol. 21(3), pp. 227-235.
Arnal et al., "Tissue specificity of the membrane vs nuclear actions of estrogen receptor alpha: insights from targeted mutations in mouse models," Archives of Cardiovascular Diseases Supplements, (Apr. 2016) vol. 8, 99-217, Abstract 0333.
Bagot et al., "The effect of estrone on thrombin generation may explain the different thrombotic risk between oral and transdermal hormone replacement therapy", J Thromb Haemost., 8(8):1736-1744 (2010).
Bennink et al., "Estetrol (E4), the forgotten fetal steroid", 9th European Congress of Endocrinology Meeting Abstract No. S16,2, Endocrine Abstracts, vol. No. 14 (2007).
Bennink et al., "Estetrol review: profile and potential clinical applications," Climacteric (2008) vol. 11, Suppl. 1, pp. 47-58.
Bennink et al., "Pharmacodynamic effects of the fetal estrogen estetrol in postmenopausal women: results from a multiple-rising-dose study," (2017) Menopause 24(6), pp. 677-685.
Bennink et al., "Pharmacokinetics of the fetal estrogen estetrol in a multiple-rising-dose study in postmenopausal women," (2017) Climacteric.20(3), pp. 285-289.
Bianchi, "Estetrol: Desde Un Estrogeno Fetal Hasta El Tratamiento De La Menopausia," Rev. Chil. Obstet. Ginecol., vol. 74, No. 2, pp. 123-126 (2009).
Bird et al., "Drospirenone and non-fatal venous thromboembolism: is there a risk difference by dosage of ethinyl-estradiol?" Journal of Thrombosis and Haemostasis, vol. 11, pp. 1059-1068 (2013).
Bjarnason et al., "Acute and long-term estradiol kinetics in smoking postmenopausal women," (2012) Climacteric, vol. 15(5), pp. 449-454.
Blanco-Molina, M.A. et al., "Progestin-only contraception and venous thromboembolism", Thrombosis Research, vol. No. 129, 2012, pp. e257-e262.
Bosworth et al., "Depressive symptoms, menopausal status, and climacteric symptoms in women at midlife," (2001) Psychosom Med., 63(4):603-8.
Bull et al., "Synthesis and structure-activity studies of 8a- and 9beta-analogues of 14,17-ethanoestradiol", J. Chem. Soc., Perkin Trans 1, 2000, pp. 1003-1013.
Callejo et al., "Effect of a low-dose oral contraceptive containing 20 microg ethinylestradiol and 150 microg desogestrel on dysmenorrhea", Contraception, 68(3), p. 183-188 (2003).
Chilukuri, D. et al., "Pharmaceutical Product Development: In Vitro-In Vivo Correlation", Informa Healthcare, Drugs and the Pharmaceutical Sciences, vol. No. 165, 2007, 216 pages.
Coelingh Bennink et al., "Ovulation inhibition by estetrol in an in vivo model" Contraception, 2008, vol. 77, pp. 186-190.
Coelingh Bennink Herjan J T et al., "Clinical effects of the fetal estrogen estetrol in a multiple-rising-dose study in postmenopausal women," (2016) Maturitas, Elsevier, Amsterdam, NL vol. 91, pp. 93-100, XP029649879.
Dahlback et al., "Familial thrombophilia due to a previously unrecognized mechanism characterized by poor anticoagulant response to activated protein C: prediction of a cofactor to activated protein C", Proc Natl Acad Sci U S A., 90(3), p. 1004-1008 (1993).
Davis et al., "Oral contraceptives for dysmenorrhea in adolescent girls: a randomized trial", Obstet Gynaecol, 106(1): 97-104 (2005).
De Bastos et al., "Combined oral contraceptives: venous thrombosis", Cochrane Database Syst Rev, (3):CD010813 (2014).
Dinger et al., "Effectiveness of Oral Contraceptive Pills in a Large U.S. Cohort Comparing Progestogen and Regimen", Obstet. & Gynecol., 117(1):33-40 (2011).
Dinger et al., "Oral Contraceptive Effectiveness According to Body Mass Index, Weight, Age, and Other Factors", Am. J. Obstet. Gynecol., 201:263e1-9 (2009).
Dinger et al., "Risk of venous thromboembolism and the use of dienogest- and drospirenone-containing oral contraceptives: results from a German case-control study", J Fam Plann Reprod Health Care, 36(3), 2010, pp. 123-129.
Duijkers et al., "A randomized study comparing the effect on Ovarian activity of a progestogen-only pill (POP) containing desogestrel and a new POP containing drospirenone in a 24/4 regimen", Euro. J. Contracept. & Repro. Health Care, 20(6):419-27 (2015).
Duijkers et al., "Inhibition of ovulation by administration of estetrol in combination with drospirenone or levonorgestrel: Results of a phase II dose-finding pilot study," The European Journal of Contraception and Reproductive Health Care (2015) vol. 20, pp. 476-489.
Elger et al., "Conception and pharmacodynamics profile of drospirenone", Steriods, 68(10):891-905 (2003).
Endrikat et al., "A twelve-month comparative clinical investigation of two low-dose oral contraceptives containing 20 micrograms ethinylestradiol/75 micrograms gestodene and 20 micrograms ethinylestradiol/150 micrograms desogestrel, with respect to efficacy, cycle control and tolerance", Contraception, 52(4), p. 229-235 (1995).
Erkkola et al., "Role of progestins in contraception", Acta Obstet Gynecol Scand., 84(3), pp. 207-216 (2005).
European Society of Contraception and Reproductive Health (ESC), "Estelle®; the new contraceptive pill containing the fetal estrogen estetrol (E4)", I4th Congress, 2nd Global Conference, May 4-7, 2016, Switzerland.

(56) References Cited

OTHER PUBLICATIONS

European Society of Contraception and Reproductive Health (ESC), "New molecules, applications (and regimens)—Room Sydney—Estetrol", I4th Congress, 2nd Global Conference, May 4-7, 2016, Switzerland.
Final Office Action on U.S. Appl. No. 16/323,110 dated Sep. 9, 2020.
Final Office Action on U.S. Appl. No. 16/323,110 dated Sep. 24, 2021.
Fine, P., Update on Emergency Contraception, Advances in Therapy, vol. No. 28, Issue No. 2, 2010, pp. 87-90.
Foidart, "Estelle?, Estetrol and drospirenone in oral contraception: E4 Freedom TM Phase 3 clinical study design," Presented at Eur. Soc. Contraception & Reprod. Health, 14th Cong, 2nd Global Conf. (May 5, 2016).
Foidart, "Estetrol, the first human, physiological Selective Estrogen Receptor Modulator," Presented at Eur. Soc. Contraception & Reprod. Health, 14th Cong, 2nd Global Conf. (May 5, 2016).
French, "Dysmenorrhea", Am Fam Physician, 71(2): 285-291 (2005).
Gardouh et al., "Preparation and Characterization of Mucoadhesive Buccal Film for Delivery of Meloxicam," British Journal of Pharmaceutical Research, vol. 3, No. 4, pp. 743-766 (Jun. 2013).
Haque et al., "Development of polymer-bound fast-dissolving metformin buccal film with disintegrants," International Journal of Nanomedicine, vol. 10 (Suppl. I: Challenges in biomaterials research) pp. 199-205 (Oct. 2015).
Harada, T., "Dysmenorrhea and Endometriosis in Young Women," Yonago Acta medica, vol. 56, pp. 81-84 (2013).
Harel et al., "Dysmenorrhea in adolescents and young adults: an update on pharmacological treatments and management strategies," Expert Opinion on Pharmacotherapy, vol. 13 No. 15, (Sep. 2012) pp. 2157-2170, XP055389783.
Harlow et al., "Executive summary of the Stages of Reproductive Aging Workshop 10: addressing the unfinished agenda of staging reproductive aging", Journal of Clinical Endocrinology & Metabolism, vol. No. 97, Issue No. 4, 2012, pp. 1159-1168.
Harrington et al., "Cross-sectional association of endogenous steroid hormone, sex hormone-binding globulin, and precursor steroid levels with hemostatic factor levels in postmenopausal women", J Thromb Haemost., 15(1), p. 80-90 (2017).
Heinemann et al., "International versions of the Menopause Rating Scale (MRS)", 2003, Health Qual Life Outcomes, pp. 1:28.
Heinemann et al., "The Menopause Rating Scale (MRS) as outcome measure for hormone treatment? A validation study," (2004) Health Qual Life Outcomes, pp. 2:67.
Heinemann et al., "The Menopause Rating Scale (MRS) scale: A methodological review", 2004, Health Qual Life Outcomes, pp. 2:45.
Hendrix and Alexander, "Primary dysmenorrhea treatment with a desogestrel-containing low-dose oral contraceptive", 66(6), p. 393-399 (2002).
Hilditch et al., "A menopause specific quality of life questionnaire: development and psychometric properties," (1996) Maturitas, vol. 24(3), pp. 161-175.
International Search Report and Written Opinion on PCT Appl. Ser. No. PCT/EP2019/060220 dated Jul. 11, 2019 (10 pages) (WO2019/202141).
International Search Report and Written Opinion on PCT Appl. Ser. No. PCT/EP2019/060221 dated Jul. 11, 2019 (WO2019/202142).
Jezerska, L. et al., "Particles segregation in pharmaceutical mixtures for direct tablets compression", VSB-Technical University of Ostrava, Jan. 2006, 8 pages.
Jick et al., "Risk of idiopathic cardiovascular death and nonfatal venous thromboembolism in women using oral contraceptives with differing progestagen components", Lancet, 346(8990), 1995, p. 1589-1593.
Kluft, "Effects on estrogenic and haemostatic variables of estetrol in combination with drospirenone," Presented at Eur. Soc. Contraception & Reprod. Health, 14th Cong, 2nd Global Conf. (May 5, 2016).

Kluft, C. et al., "Reduced hemostatic effects with drospirenone-based oral contraceptives containing estetrol vs. ethinyl estradiol", Contraception, vol. No. 95, Issue No. 2, 2016, pp. 140-147.
Lianmei, L et al., "Major research advances in estetrol," (2009) J Reprod Med, vol. 18(3), pp. 305-308.
Lidegaard et al., "Hormonal contraception and risk of venous thromboembolism: national follow-up study," BMJ, 339:b2890, 2009, pp. 1-8.
Lidegaard et al., "Risk of venous thromboembolism from use of oral contraceptives containing different progestogens and oestrogen doses: Danish cohort study, Sep. 2001", BMJ, 2011, 343:d6423, 15 pages.
Mawet et al., "Unique effects on hepatic function, lipid metabolism, bone and growth endocrine parameters of estetrol in combined oral contraceptives," The European Journal of Contraception and Reproductive Health Care, (2015) vol. 20, pp. 463-475.
Meeting of the Committee for Medicinal Products for Human Use (CHMP) in Mar. 2021, https://www.aemps.gob.es/informa/boletines-aemps/boletin-chmp/2021-boletinchmp/reunion-del-comite-de-medicamentos-de-uso-humano-chmp-de-marzo-2021/.
Meulenbroeks et al: "21+7 day versus 24+4 day monophasic regimens of combined oral contraceptives for contraception (Protocol)", Cochrane database of systematic reviews, Issue 7, art. No. CD011781, 2015.
Nath and Sitruk-Ware, "Pharmacology and clinical applications of selective estrogen receptor modulators", Climacteric, vol. No. 12, Issue No. 3, Jun. 2009, pp. 188-205.
Notelovitz et al., "Initial 17β-Estradiol Dose for Treating Vasomotor Symptoms," (2000) Obstetrics and Gynaecology, vol. 95(5), pp. 726-731.
Notice of Allowance dated Aug. 15, 2019 in U.S. Appl. No. 16/025,719 (US 2019-0125759).
Notice of Allowance dated Jan. 7, 2020, in U.S. Appl. No. 16/025,719 (US 2019-0125759).
Notice of Allowance on U.S. Appl. No. 17/048,538 dated Aug. 10, 2022.
Notice of Allowance on U.S. Appl. No. 17/048,540 dated Aug. 8, 2022.
Office Action dated May 1, 2019 in U.S. Appl. No. 15/737,233 (US 2018-0185271).
Office Action dated May 17, 2019 in U.S. Appl. No. 15/737,189 (US 2018-0153801).
Office Action dated May 25, 2021, in U.S. Appl. No. 16/573,611 (US 2020-0046729).
Office Action dated Nov. 4, 2019, in U.S. Appl. No. 15/737,233 (US 2018-0185271).
Osayande, A. et al., "Diagnosis and Initial Management of Dysmenorrhea", American Family Physician, vol. No. 89, Issue No. 5, Mar. 1, 2014, pp. 341-346.
Pinkerton, JoAnn V., https://www.msdmanuals.com/es-do/professional/ginecolog%C3%ADa-yobstetricia/ anomal%C3%ADas-menstruales/dismenorrea (Dec. 2020).
Poort et al., "A common genetic variation in the 3'-untranslated region of the prothrombin gene is associated with elevated plasma prothrombin levels and an increase in venous thrombosis", Blood, 88(10), p. 3698-3703 (1996).
Portman et al., "Genitourinary syndrome of menopause: new terminology for vulvovaginal atrophy from the International Society for the Study of Women's Sexual Health and the North American Menopause Society," (2014) Menopause, vol. 21(10), pp. 1063-1068.
Prandoni, P. et al., "An Association between Atherosclerosis and Venous Thrombosis", The New England Journal of Medicine, vol. No. 348, Issue No. 15, Apr. 10, 2003, pp. 1435-1441.
Proctor and Farquhar, "Dysmenorrhoea", Clin Evid, 9, p. 1994-2013 (2003).
Radtke, J. et al., "The Menopause-Specific Quality of Life (MENQOL) Questionnaire: Psychometric Evaluation among Breast Cancer Survivors", Menopause, vol. No 18, Issue No. 3, Mar. 2011, pp. 289-295.
Rodstrom et al., "A longitudinal study of the treatment of 25 hot flushes: the population study of women in Gothenburg during a quarter of a century," (2002) Menopause, vol. 9(3), pp. 156-161.

(56) References Cited

OTHER PUBLICATIONS

Rosenbaum et al., "Inhibition of ovulation by a novel progestogen (drospirenone) alone or in combination with ethinylestradiol", Euro. J. Contracept. & Repro. Health Care, 5(1):14-24 (2000).
Rosing et al., "Oral contraceptives and venous thrombosis: different sensitivities to activated protein C in women using second- and third-generation oral contraceptives", Br J Haematol., 97(1), p. 233-238 (Apr. 1, 1997).
Santoro, "Symptoms of menopause: hot flushes," (2008) Clin Obstet Gynecol, vol. 51(3), pp. 539-548.
Savjani et al., "Drug solubility: importance and enhancement techniques", ISRN Pharm., 2012: 195727.
Shulman, "Estelle, Estetrol: changing hormones in advancing oral contraception," Presented at Eur. Soc. Contraception & Reprod. Health, 14th Cong, 2nd Global Conf. (May 5, 2016).
Sidney et al., "Recent combined hormonal contraceptives (CHCs) and the risk of thromboembolism and other cardiovascular events in new users", Contraception, 87(1), p. 93-100 (2013).
Simon et al., "Menopausal hormone therapy for vasomotor symptoms: balancing the risks and benefits with ultra-low doses of estrogen," (2007) Expert Opin Investig Drugs, vol. 16(12), pp. 2005-2020.
Simoni et al., "The Discovery of Estrone, Estriol, and Estradiol and the Biochemical Study of Reproduction. The Work of Edward Adelbert Doisy", J. Biol. Chem, vol. 277, No. 28, e17, 2002, 2 pages.
Spitzer et al., "Third generation oral contraceptives and risk of venous thromboembolic disorders: an international case-control study. Transnational Research Group on Oral Contraceptives and the Health of Young Women", BMJ, 312(7023), p. 83-88 (1996).
Stanczyk, F. et al., "Progestogens used in postmenopausal hormone therapy: differences in their pharmacological properties, intracellular actions, and clinical effects", Endocrine Reviews, vol. No. 34, Issue No. 2, Apr. 2013, pp. 171-208.
Strowitzki et al., "Efficacy of ethinylestradiol 20 ug/drospirenone 3 mg in a flexible extended regimen in women with moderate-to-severe primary dysmenorrhea: an open-label, multicenter, ramdomized, controlled study," J. Fam. Plann. Reprod. Health Care (2012) vol. 38, pp. 94-101.
Sundell et al., "Factors influencing the prevalence and severity of dysmenorrhoea in young women.", Br J Obstet Gynaecol, 97(7), p. 588-594 (Jul. 1, 1990).
Tchaicovski and Rosing, "Mechanisms of estrogen-induced venous thromboembolism", Thromb Res., 126(1):5-11 (Feb. 16, 2010).
The American College of Obstetricians and Gynecologists, "Committee Opinion No. 540: Risk of Venous Thromboembolism Among Users of Drospirenone-Containing Oral Contraceptive Pills", Nov. 2012, 4 pages.
The European Agency for the Evaluation of Medicinal Products, "CPMP Public Assessment Report—Combined oral contraceptives and venous thromboembolism", Sep. 2001, 7 pages.
U.S. Department of Health & Human Services—National Institutes of Health—National Center for Advancing Translational Sciences, "Estetrol Monohydrate", retrieved from https://drugs.ncats.io/substance/KC3GI9UM9V (First Approved in 2001).
U.S. Department of Health and Human Services—Food and Drug Administration—Center for Drug Evaluation and Research (CDER), "SUPAC: Manufacturing Equipment Addendum: Guidance for Industry", Pharmaceutical Quality/CMC, Dec. 2014, 33 pages.
Utian et al., "Comparative controlled trial of a novel oral estrogen therapy, estradiol acetate, for relief of menopause symptoms," (2005) Menopause, vol. 12(6), pp. 708-715.
Visser et al., "Clinical applications for estetrol," Journal of Steroid Biochemistry and Molecular Biology 114 (2009) 85-89.
Vlieg et al., "The venous thrombotic risk of oral contraceptives, effects of oestrogen dose and progestogen type: results of the MEGA case-control study", BMJ, 2009, 339:b2921, 8 pages.
Williams et al., "Strategies to address low drug solubility in discovery and development," (2013) Pharmacological Reviews, vol. 65(1), pp. 416-445.
Winkler et al., "Cycle control, quality of life and acne with two low-dose oral contraceptives containing 20 microg ethinylestradiol", Contraception, 96(6), 2004, pp. 469-476.
Wong et al., "Oral contraceptive pill as treatment for primary dysmenorrhoea", Cochrane Database Syst Rev., CD002120, 2009.
Wto, "Venous thromboembolic disease and combined oral contraceptives: results of international multicentre case-control study", Lancet, 346(8990), p. 1575-1582 (1995).
Ylikorkala and Dawood, "New concepts in dysmenorrhea", Am J Obstet Gynecol, 130(7), 1978, p. 833-847.
Zhang and Wan Po, "Efficacy of minor analgesics in primary dysmenorrhoea: a systematic review", Br J Obstet Gynaecol, vol. 130, Issue No. 7, Jul. 1998, pp. 780-789.
U.S. Appl. No. 17/893,999, filed Aug. 23, 2022, Estetra SRL.
U.S. Appl. No. 17/900,576, filed Aug. 31, 2022, Estetra SRL.
U.S. Appl. No. 17/963,712, filed Oct. 11, 2022, Estetra SRL.
U.S. Appl. No. 17/972,403, filed Oct. 24, 2022, Estetra SRL.
Duavive (bazedoxifene), Eur. Med. Agency, Dec. 2014.
E4 Relief, www.e4relief.com/cz, Wayback Machine snapshot of webpage from Jan. 2, 2017.
NCT02834312, "E4Relief (Response to Estetrol in Life Improvement for MEnopausal-associated Hot Flushes)," ClinicalTrials.Gov (Jan. 25, 2018).
U.S. Appl. No. 17/504,087, filed Oct. 18, 2021, Jaspart et al.
U.S. Appl. No. 17/701,588, filed Mar. 22, 2022, Jean-Michel Foidart.
"Illustrated Glossary of Organic Chemistry", retrieved from http://www.chem.ucla.edu/~harding/IGOC/H/hydrate.html printed Apr. 19, 2022.
Abot et al., The uterine and vascular actions of estetrol delineate a distinctive profile of estrogen receptor alpha modulation, uncoupling nuclear and membrane activation, EMBO Molecular Medicine, vol. 6, No. 10, 2014 (19 pages).
Al-Jefout et al., "Continuous Norethisterone Acetate versus Cyclical Drospirenone 3 mg/Ethinyl Estradiol 20 ug for the Management of Primary Dysmenorrhea in Young Adult Women," Journal of Pediatric and Adolescent Gynecology, vol. 29, No. 2, pp. 143-147, XP029421056 (Sep. 2015).
Andersch and Milsom, "An epidemiologic study of young women with dysmenorrhea", Am J Obstet Gynecol, 144(6), p. 655-660 (1982).
Anderson and Spencer, "Risk factors for venous thromboembolism", Circulation, vol. No. 107, 2003, pp. I-9-I-16.
Anderson et al., "Effects of conjugated equine estrogen in postmenopausal women with hysterectomy: the Women's Health Initiative randomized controlled trial", JAMA (2004), vol. 291(14), pp. 1701-1712.
Apter et al., "Bleeding pattern and cycle control with estetrol-containing combined oral contraceptives: results from a phase II, randomized, dose-finding study (FIESTA)," Contraception 94 (2016) pp. 366-373.

\* cited by examiner

METHOD FOR PREVENTING PREGNANCY

CROSS-REFERENCE TO RELATED APPLICATIONS

The present application is a continuation of application Ser. No. 16/323,110, filed Feb. 4, 2019, which is the U.S. National Stage of International Application No. PCT/EP2017/069908, filed Aug. 7, 2017, and claims priority to European Patent Application No. 16183025.2, filed Aug. 5, 2016, and International Application No. PCT/EP2016/076104, filed Oct. 28, 2016.

FIELD OF THE INVENTION

The present invention relates to a method of alleviating the symptoms of dysmenorrhea in a person, comprising administering to said person an effective amount of an estrogenic component. More particularly the estrogenic component is an estetrol component, as further defined herein, and the method enjoys a favourable side-effect profile compared to currently available methods.

BACKGROUND ART

Dysmenorrhea is a medical condition characterized by the presence of recurrent, crampy, lower abdominal pain that occurs during menses. Most women begin having dysmenorrhea during adolescence, usually within four to five years of the first menstrual period. Painful periods become less common as women age. For clinical purposes, dysmenorrhea is divided into two broad categories, primary and secondary dysmenorrhea. Primary dysmenorrhea refers to the presence of recurrent, crampy, lower abdominal pain that occurs during menses in the absence of demonstrable disease that could account for these symptoms.

Secondary dysmenorrhea has the same clinical features, but occurs in women with a disorder that could account for their symptoms, such as endometriosis, adenomyosis, or uterine fibroids.

Primary Dysmenorrhea

It is known that 50 to 90 percent of reproductive-aged women describe experiencing painful menstrual periods. The majority of these women are young and have primary dysmenorrhea. The prevalence of primary dysmenorrhea decreases with advancing age (Sundell G. et al.; *Br J Obstet Gynaecol* 1990; 97:588).

Primary dysmenorrhea has been associated with alterations in prostaglandin synthesis and metabolism. Prostaglandins released from endometrial sloughing at the beginning of menses play a major role in inducing contractions (Ylikorkala O, Dawood M Y.; *Am J Obstet Gynecol* 1978; 130: 833).

The pain starts one to two days before or with the onset of menstrual bleeding and then gradually diminishes over 12 to 72 hours. It is recurrent, occurring in most, if not all, menstrual cycles. The pain is usually crampy and intermittently intense, but may be a continuous dull ache. It is usually confined to the lower abdomen and suprapubic area. Although the pain is usually strongest in the midline, some women also have severe back and/or thigh pain.

The severity of the pain ranges from mild to severe (Table 1 below) (Andersch B, Milsom I.; *Am J Obstet Gynecol* 1982; 144:655).

As used herein, the "dysmenorrhea symptoms grade" corresponds to the score obtained by applying the assessment presented in Table 1.

TABLE 1

Verbal multidimensional scoring system for assessment of dysmenorrhea

| Grade | Working Ability | Systemic Symptoms | Analgesics |
|---|---|---|---|
| Grade 0: Menstruation is not painful and daily activity is unaffected | Unaffected | None | None required |
| Grade 1: Menstruation is painful but seldom inhibits normal activity; analgesics are seldom required; mild pain | Rarely affected | None | Rarely required |
| Grade 2: Daily activity is affected; analgesics required and give sufficient relief so that absence from school is unusual; moderate pain | Moderately affected | Few | Required |
| Grade 3: Activity clearly inhibited; poor effect of analgesics; vegetative symptoms (headache, fatigue, vomiting, and diarrhea); severe pain | Clearly inhibited | Apparent | Poor effect |

It is important to note that there are no physical findings associated with primary dysmenorrhea and that primary dysmenorrhea is not associated with any laboratory abnormalities or abnormal findings on imaging studies. Diagnosis should therefore ascertain that the patient has no evidence of other disorders that could account for the pain. In particular disorders such as endometriosis, adenomyosis, fibroids, ovarian cysts, among others, have been associated with secondary dysmenorrhea.

Treatment Options for Primary Dysmenorrhea

Nonsteroidal anti-inflammatory drugs (NSAIDs) are considered the first line of therapy (Proctor M, Farquhar C; *Clin Evid* 2003; :1994-Zhang W Y, Li Wan Po A.; *Br J Obstet Gynaecol* 1998; 105:780-French L.; *Am Fam Physician* 2005; 71:285).

NSAIDs should be started at the onset of menses and continued for the first one to two days of the menstrual cycle or for the usual duration of crampy pain. Patients with severe symptoms should begin taking NSAIDs one to two days prior to the onset of menses.

Combined Oral Contraceptive pills (COCs) can be given to patients who fail to respond to or cannot tolerate NSAIDs (Davis A R, et al.; *Obstet Gynecol* 2005; 106:97). COCs prevent menstrual pain by suppressing ovulation, thereby decreasing uterine prostaglandin levels. An additional mechanism may result from the reduction of menstrual flow after several months of use.

In a sexually active female, COCs may be considered for first-line of therapy because they serve a dual purpose: prevention of both pregnancy and dysmenorrhea.

A systematic review of randomized trials of estrogen-progestin contraceptive pills for treatment of primary dysmenorrhea reported a significant benefit of treatment (pooled OR of 2.99, 95% CI 1.76-5.07) (Wong C L, et al.; *Cochrane Database Syst Rev* 2009; :CD002120).

Few trials compared different doses of estrogen for treatment of primary dysmenorrhea; the review concluded pain relief was similar for low (≤35 mcg) and medium (>35 mcg) estrogen doses and there was no clear difference in efficacy among the different pill preparations.

However, additional data from observational studies and other randomized trials have demonstrated efficacy of very low dose estrogen pills for treatment of dysmenorrhea (Davis A R, et al.; *Obstet Gynecol* 2005; 106:97-Callejo J, et al.; *Contraception* 2003; 68:183-Winkler U H, et al.;

Contraception 2004; 69:469-Endrikat J, et al.; *Contraception* 1995; 52:229-Hendrix S L, Alexander N J.; *Contraception* 2002; 66:393).

All these approaches relied on COCs employing synthetic estrogens such as ethinyl estradiol (EE), however. In such a case, there is a (dose dependent) risk of undesirable side-effects, such as thromboembolism, fluid retention, nausea, bloating, cholelithiasis, headache and breast pain.

Of particular importance is the fact that estrogens participate in the regulation of the synthesis of a variety of proteins in the liver, such as angiotensinogen, Sex Hormone Binding Globulin (SHBG), ceruloplasmin, Corticosteroid Binding Globulin (CBG), some coagulation factors, coagulation inhibitors or fibrinolysis markers. Changes in these haemostasis markers under the influence of strong estrogens such as EE may collectively contribute to create an imbalance between pro-coagulation and anti-coagulation factors which can enhance the risks of Venous ThromboEmbolism (VTE) events.

SHBG plasma levels are a reliable marker of the influence of an estrogen on the synthesis of these proteins by liver cells. This means that a correlation could exist between the level of SHBG induced by a specific COC and the risk of VTE associated with that COC (Odlind V, et al.; *Acta Obstet Gynecol Scand* 2002; 81:482).

Although cohort studies performed on a sufficient number of subjects are required to evaluate the risk of VTE with a specific COC, different haemostatic markers and carrier proteins (such as SHBG) can be measured to estimate this risk on a limited number of subjects.

There thus remains a need for a therapeutic approach which, on the one hand, has as little side effects as possible, but on the other hand proves very efficient in the management of dysmenorrhea.

SUMMARY OF THE INVENTION

The present invention relates to a method of alleviating the symptoms of dysmenorrhea in a person, comprising administering to said person an effective amount of an estrogenic component. More particularly the estrogenic component is an estetrol component, as further defined herein, and the method enjoys a favourable side-effect profile compared to currently available methods.

In one aspect of the method, one or more of the number, the frequency and the severity of treatment-related side effects is reduced, compared to other dysmenorrhea treatments of similar efficacy.

In one embodiment of the invention, the number, frequency and/or severity of VTE events is reduced, compared to other dysmenorrhea treatments of similar efficacy.

In another embodiment of the invention, no haemostatic change that exceeds the boundaries of the normal range, as further defined herein, occurs upon administration of the compositions of the invention.

In a further embodiment of the invention, the number, frequency and/or severity of headaches is reduced, compared to other dysmenorrhea treatments of similar efficacy.

In yet another embodiment of the invention, the number, frequency and/or severity of breast pain events is reduced, compared to other dysmenorrhea treatments of similar efficacy.

In one embodiment of the invention, the method involves the administration of an effective amount of an estrogenic component and of a progestogenic component.

In some embodiments of the invention, the estrogenic and the progestogenic components are included in a single dosage unit. In further embodiments, the dosage unit is a daily dosage unit.

In further embodiments, the progestogenic component is drospirenone and that component is used at a daily dose of from 0.5 mg to 10 mg, preferably at a daily dose of from 1 mg to 4 mg.

In yet further embodiments, the estrogenic component is used at a daily dose of from 1 mg to 40 mg, preferably at a daily dose of from 5 mg to 25 mg, even more preferably at a daily dose of from 10 mg to 20 mg. In particular embodiments, the estrogenic component is estetrol monohydrate.

In a specific embodiment of the invention, the estrogenic component is estetrol monohydrate at a daily dose of about 15 mg and the progestogenic component is drospirenone at a daily dose of about 3 mg.

The present method employs an estrogenic component which is a natural estrogen (i.e. found in nature) and a biogenic estrogen (i.e. occurring naturally in the human body).

Because biogenic estrogens are naturally present in the fetal and female body, a good tolerability and safety profile are observed, particularly if the serum levels resulting from the exogenous administration of such estrogens do not substantially exceed naturally occurring concentrations. A direct consequence of this good tolerability is the favourable side-effect profile obtained with the method of the invention compared to other methods.

DETAILED DESCRIPTION OF THE INVENTION

Definitions

The term "estrogenic component" as used throughout this document encompasses substances that are capable of triggering an estrogenic response in vivo, as well as precursors that are capable of liberating such an estrogenic component in vivo when used in accordance with the present invention. In order for estrogenic components to trigger such a response they normally have to bind to an estrogen receptor, which receptors are found in various tissues within the mammalian body.

The estrogenic component of the present invention preferably is an estetrol component. The term "estetrol component", as used throughout this document, encompasses substances selected from the group consisting of estetrol, esters of estetrol wherein the hydrogen atom of at least one of the hydroxyl groups has been substituted by an acyl radical of a hydrocarbon carboxylic, sulfonic acid or sulfamic acid of 1-25 carbon atoms; and combinations thereof. Even more preferably, the estetrol component is estetrol (including estetrol hydrates). Most preferably, the estetrol component contained in the dosage unit is estetrol monohydrate.

The term "progestogenic component" is defined as a substance that is capable of triggering a progestogenic response in vivo or a precursor which is capable of liberating such a substance in vivo. Usually progestogenic components are capable of binding to a progestogen receptor.

"About" as used herein referring to a measurable value such as a parameter, an amount, a temporal duration, and the like, is meant to encompass variations of +/−10% or less, more preferably +/−5% or less, even more preferably +/−1% or less of and from the specified value, in so far such variations are appropriate to perform in the disclosed invention. However, it is to be understood that the value to which the modifier "about" refers is itself also specifically disclosed.

The term "an effective amount" refers to an amount necessary to obtain a physiological effect. The physiological effect may be achieved by one dose or by repeated doses. In particular, "an effective amount" refers to an amount which is effective in reducing, eliminating, treating or controlling the symptoms of dysmenorrhea. The term "controlling" is intended to refer to all processes wherein there may be a slowing, interrupting, arresting, or stopping of the progression of dysmenorrhea, but does not necessarily indicate a total elimination of dysmenorrhea, and is intended to include prophylactic treatment and chronic use.

As illustrated in Example 5, the present method of alleviating the symptoms of dysmenorrhea has proved surprisingly efficient despite the low daily dosage employed. Without wishing to be bound by theory, the present inventors believe that the superiority of the present method is in part due to the surprising effect of the estetrol component which is capable of mitigating dysmenorrhea on its own, as illustrated in the clinical results presented in Example 1.

It is indeed the case that while the administration of low doses of estrogen are known to decrease catamenial migraine, no such effect has ever been reported for dysmenorrhea. The uniqueness of the present finding that the estetrol component is capable of alleviating the symptoms of dysmenorrhea allows to decrease those symptoms when the estetrol component is administered alone according to the method of the invention. In one particular embodiment of the method, the estetrol component is administered alone during the progestin-free interval of the method of treatment according to the invention, as further described below.

This is all the more unexpected that a substantial number of scientific publications have characterized estetrol as a weak estrogen, therefore at the doses employed in the clinical trials reported in the examples it was not foreseen that such a positive effect on the management of dysmenorrhea symptoms would be observed.

Again without wishing to be bound by theory, the present inventors believe that the superiority of the present method is also due to the mild stimulatory effect that the estetrol component has on the endometrium, especially by comparison with the stronger stimulatory effect of ethinyl estradiol, which is the estrogen used in a large number of COCs. As a result, it was found that endometrial thickness was strongly diminished upon administration of the compositions of the invention. The thin endometrium contains relatively small amounts of arachidonic acid, the substrate for most prostaglandin synthesis. As a result of these changes in the endometrium, the compositions of the invention reduce both menstrual flow and uterine contractions at menses, thereby decreasing dysmenorrhea.

Besides, the method according to the invention was found to suppress ovulation in 100% of patients and suppression of ovulation is decreasing uterine prostaglandin levels.

In a comparative study, it was surprisingly found that a combination of estetrol with drospirenone as the progestogenic component was more efficient at managing the symptoms of dysmenorrhea than a combination of estetrol with levonorgestrel as the progestogenic component. This is illustrated by the results of the clinical trial reported in Example 2.

Another important benefit of the present estetrol component is derived from its relative insensitivity to interactions with other drugs (drug-drug interactions). It is well known that certain drugs may decrease the effectiveness of estrogens, such as ethinyl estradiol, and other drugs may enhance their activity, resulting in possible increased side-effects. Similarly estrogens may interfere with the metabolism of other drugs. In general, the effect of other drugs on estrogens is due to interference with the absorption, metabolism or excretion of these estrogens, whereas the effect of estrogens on other drugs is due to competition for metabolic pathways.

The clinically most significant group of estrogen-drug interactions occurs with drugs that may induce hepatic microsomal enzymes which may decrease estrogen plasma levels below therapeutic level (for example, anticonvulsant agents; phenytoin, primidone, barbiturates, carbamazepine, ethosuximide, and methosuximide; antituberculous drugs such as rifampin; antifungal drugs such as griseofulvin). The present estrogenic substances are not dependent on up- and downregulation of microsomal liver enzymes (e.g. P450's) and also are not sensitive to competition with other P450 substrates. Similarly, they do not interfere significantly in the metabolism of other drugs.

In particular, estetrol at a high concentration of 10 µmol/l does not inhibit (less than 10%) the major cytochrome P450 enzymes (CYP1A2, CYP2C9, CYP2C19, CYP2D6 and CYP3A4) unlike estradiol. Indeed, estradiol exerts a substantial inhibitory effect on CYP2C19 and CYP1A2 of 63% and 19%, respectively. Similarly, ethinyl estradiol, which is the estrogen used in a large number of COCs, exerts a substantial inhibitory effect on CYP2C19 and CYP3A4 of 82% and 45%, respectively.

The above observations serve to explain why the estetrol component of the invention hardly suffer from drug-drug interactions and thus produce a very consistent, i.e. predictable, impact. Thus, the efficacy of the estrogenic substances of the invention is highly reliable.

Additionally, the terminal half-life of the naturally occurring estrogens ranges from 2 to 14 hours while estetrol is characterized by a terminal half-life of 31.7 hours.

Consequently, the use of estetrol in the method of the invention allows for a more than 24-hour coverage of the receptors by the treatment. This pharmacokinetic property enhances the efficacy of the product even in case of low treatment compliance by the user.

It has to be noted that when estetrol (E4) is associated with 3 mg drospirenone (DRSP) or 150 µg Levonorgestrel (LNG), the bleeding profile and the cycle control is improved in comparison to other combined oral contraceptives using a physiological estrogen, namely estradiol-valerate (E2V) or estradiol (E2).

In a study evaluating the bleeding pattern and cycle control of different E4/DRSP or E4/LNG combinations in comparison to a marketed quadriphasic combined oral contraceptive containing E2V and desogestrel (DSG), the combinations of 15 mg E4/DRSP and the combination 20 mg E4/LNG were both associated with a lower incidence of unscheduled bleeding/spotting days than the comparator. In addition, absence of withdrawal bleeding (also called amenorrhea) was much lower with the E4 containing preparations, particularly when E4 is associated with DRSP, than with the comparator. Finally, mean number of days with unscheduled bleeding/spotting by cycle was also lower with the combination of 15 mg E4/DRSP in comparison with the E2V/DNG preparation. This was also the case when compared to publicly available data on a marketed combined oral contraceptive containing E2 as estrogen in association with nomegestrol acetate (NOMAC).

Besides, the daily use of currently marketed estrogens (ethinylestradiol (EE), E2, E2V, conjugated equine estrogens) is associated with a dose-proportional increase in triglycerides levels. In the human body, high levels of triglycerides in the bloodstream have been linked to atherosclerosis and, by extension, the risk of heart disease and stroke. In the opposite to the currently available estrogens, E4 minimally increases triglycerides levels even at higher dosages.

Finally, the use of combined contraceptives have been associated with an increased risk in venous thromboembolic events (VTEs). In comparison with non-users, the use of second generation COCs multiply by 2 the risk of VTE and the use of 3rd and 4th COCs multiply the risk by 4. The absolute risk of VTE associated with the use of a specific combined contraceptive can only be assessed during very large epidemiological trials. However, and as requested by the European Medicinal Agency, several surrogate markers of the VTE risk can be measured in smaller clinical settings to estimate the risk.

As illustrated in Example 4, from the clinical results obtained with combinations of E4 and DRSP or LNG, the changes in the surrogate markers of VTE were minimal in comparison to the changes observed with Yaz® (a combination of 20 µg EE and 3 mg DRSP). DRSP is a fourth generation progestin associated with the highest risk of VTE when it is combined with the synthetic estrogen EE. Accordingly, the changes in the surrogate markers of VTE seen with a combination of EE and DRSP are substantial. In comparison, the changes observed with the E4 combinations are minimal even when DRSP is associated to the estrogen. For example, the SHBG plasma level changes observed when E4 was associated with 3 mg DRSP were considerably lower (mean percentage change of 7.9% for the 5 mg E4/3 mg DRSP group and of 44.5% for the 10 mg E4/3 mg DRSP group at treatment cycle 3) than the SHBG increases observed with a combination of 20 µg EE and 3 mg DRSP (mean percentage change of 306.3% for Yaz® at treatment cycle 3). The same positive pattern of change was observed with the 14 additional surrogate markers of VTE measured in this trial.

Methods of Treatment

The present methods usually employ uninterrupted oral administration of the estrogenic component and the progestogenic component during a period of at least 10 days, preferably of at least 20 days.

The term "uninterrupted" as used in here, means that the components are administered at relatively regular intervals, with no (therapeutically) significant interruptions. Naturally, minor interruptions may occur that do not affect the overall effectiveness of the present method, and indeed such aberrations are encompassed by the present invention. In a preferred embodiment, and more arithmetically, the administration regimen is deemed to be continuous if the longest interval between 2 subsequent administrations is not more than 3.5 times as long as the average interval. Even more preferably said longest interval is not more than 2.5 times, most preferably not more than 1.5 times as long as the average interval.

In the present method, the estrogenic and progestogenic components may be administered in separate dosage units. However, it is also possible and indeed very convenient to combine these two components into a single dosage unit.

In the method according to the present invention the combination of the progestogenic and estrogenic component is suitably administered uninterruptedly during a period of at least 10 days.

The invention may suitably be reduced to practice in the form of a variety of administration methods that are known to the person skilled in the art. Amongst these methods are the so called "combined" methods. The combined methods make use of monophasic preparations, which contain dosage units with a constant amount of an estrogen and a progestogen, or bi- or triphasic preparations which have varying levels of estrogen and progestogen; in most cases consisting of relatively constant levels of estrogen with a step-wise increase in progestogen throughout the cycle. The combined methods have in common that they are based on a regimen which involves an administration-free interval of about 7 days whereby withdrawal bleeding, simulating the natural menses, occurs. Thus 21 day intervals of hormone administration alternate with 7 days during which no hormones are administered.

In a preferred embodiment of the method of the invention, an administration-free interval of about 4 days is used. In this embodiment, a 24 day interval of hormone administration alternates with 4 days during which no hormones are administered.

In yet another preferred embodiment of the method of the invention, a 24 day interval of hormone administration during which an estrogenic component and a progestogenic component are administered alternates with 4 days during which only an estrogenic component is administered (from day 25 to day 28).

As an alternative to the aforementioned combined methods, the so called "sequential" method has been proposed. Typical of the sequential method is that it comprises two consecutive phases, i.e. one phase during which estrogen and no progestogen is administered and another phase during which a combination of estrogen and progestogen is administered. The first sequential methods, like the aforementioned combined methods, made use of an administration free interval of about 7 days. More recently, sequential methods have been proposed which do not include an administration-free (or placebo) period, meaning that estrogen is administered throughout the full cycle and that progestogen is co-administered during only part of that cycle. WO 95/17895 (Ehrlich et al.) describes such an uninterrupted sequential method.

Yet another example of a method which is encompassed by the present invention is the so called "continuous combined" method, which is a particular version of the combined method that uses uninterrupted combined administration of a progestogenic and an estrogenic component during a prolonged period of time, e.g. more than 50 days. In contrast to ordinary combined and sequential methods, no regular menses occur in the continuous combined method as the continuous administration of progestogen in the indicated amounts induces amenorrhoea.

In one embodiment of the invention, which relates to the continuous combined method, the present method comprises the uninterrupted oral administration of the combination of the estrogenic component and the progestogenic component during a period of at least 28, preferably at least 60 days.

In one specific embodiment of the continuous combined method according to the invention, one tablet comprising the combination of the estrogenic component and of the progestogenic component is initially taken daily for at least about 24 consecutive days. Subsequently, e.g. during days 25 to 120, the patient may decide to take a tablet-free break of about 4 days. In any case, an about 4-day tablet-free break has to be taken after about 120 days of continuous tablet administration. After each tablet-free break, a new cycle starts with a minimum of about 24 days and a maximum of about 120 days of continuous administration.

In another embodiment of the invention, which relates to sequential and combined methods that employ a significant administration-free interval, the method of the invention comprises an interval of at least 2 days, preferably from 3-9 days, most preferably from 5-8 days, during which no progestogenic component and no estrogenic component is administered and wherein the resulting decrease in serum concentration of the progestogenic component and the estrogenic component induces menses.

Yet another embodiment of the invention, which concerns a sequential method without a significant pause, is characterised in that it comprises the uninterrupted oral administration of the estrogenic component during a period of at least 28 days, preferably at least 60 days, and in that, following the combined administration of the estrogenic component and the progestogenic component, the estrogenic component and no progestogenic component are administered during 3-18 consecutive days, preferably during 5-16 consecutive days and the resulting decrease in serum concentration of the progestogenic component should normally be sufficient to induce menses.

According to the present invention, the composition for use in a method of alleviating the symptoms of dysmenorrhea is capable of reducing the number, frequency and/or severity of adverse side effects including VTE, headache, breast pain, and the like, preferably including VTE, headache, and breast pain, more preferably including VTE and headache, and most preferably including VTE. The composition according to the present invention is particularly useful for effective treatment of the symptoms of dysmenorrhea while reducing the side effect of VTE at a significantly low frequency and severity.

In a particular embodiment of the invention, the method does not cause haemostatic change that exceeds the boundaries of the normal range. As used herein, "haemostatic change" is defined as the variation, upon administration of the compositions according to the invention, of the plasma level of one or more markers selected from: Sex Hormone Binding Globulin (SHBG), free tissue factor pathway inhibitor (free TFPI), free and total protein-S, protein-S activity, Corticosteroid Binding Globulin (CBG), Ceruloplasmin, antithrombin III, activated protein C (APC) resistance (e.g. APTT-based APCr or ETP-based APCr), Protein-C activity, D-dimer, Prothrombin, Prothrombin fragment 1+2, Factor VII, Factor VIII, von Willebrand factor, Factor II, PAI-1, tissue-type plasminogen (t-PA), plasminogen, E-selectin, and fibrinogen.

The above-listed markers are well-known to the skilled person and methods for the determination of their level are within the common general knowledge of the skilled person.

As used herein, the "normal range", when referring to levels of haemostatic markers, refers to the prediction interval that 95% of the population fall into.

In one embodiment of the invention, the method does not cause haemostatic change exceeding the boundaries of the normal range after one cycle of treatment, preferably the method does not cause haemostatic change exceeding the boundaries of the normal range after two cycles of treatment, even more preferably the method does not cause haemostatic change exceeding the boundaries of the normal range after three cycles of treatment.

In another particular embodiment of the invention, the method does not cause a change in the level of protein-S which exceeds the boundaries of the normal range.

In another particular embodiment of the invention, the method does not cause a change in the level of free TFPI which exceeds the boundaries of the normal range.

Compositions

The estrogenic component of the present invention preferably is an estetrol component, which encompasses substances selected from the group consisting of estetrol, esters of estetrol wherein the hydrogen atom of at least one of the hydroxyl groups has been substituted by an acyl radical of a hydrocarbon carboxylic, sulfonic acid or sulfamic acid of 1-25 carbon atoms; and combinations thereof. More preferably, the estetrol component is estetrol (including estetrol hydrates). Most preferably, the estetrol component contained in the dosage unit is estetrol monohydrate.

The estetrol component of the invention may be used at a daily dose of from 0.1 mg to 100 mg. Preferably, the estetrol component of the invention is used at a daily dose of from 1 mg to 40 mg. Even more preferably, the estetrol component of the invention is used at a daily dose of from 5 mg to 25 mg. Still more preferably, the estetrol component of the invention is used at a daily dose of from 10 mg to 20 mg.

In a most preferred embodiment, the estetrol component of the invention is used at a daily dose of about 15 mg.

In other embodiments, dosages may be variable throughout the cycle (bi-phasic, tri-phasic or quadriphasic administration).

In a particularly preferred embodiment of the invention the pharmaceutical composition according to invention is designed for daily administration, i.e. it represents a daily dosage unit.

In the case of oral administration, the oral dosage unit according to the invention is preferably a solid or semi-solid dosage form such as tablets, capsules, cachets, pellets, pills, powders and granules. The term "solid or semi-solid dosage form" also encompasses capsules that contain a liquid, e.g. an oil, in which the present estetrol component is dissolved or dispersed. Tablets and equivalent solid and semi-solid dosage forms can suitably contain materials such as binders (e.g. hydroxypropylmethyl cellulose, polyvinyl pyrrolidone, other cellulosic materials and starch), diluents (e.g. lactose and other sugars, starch, dicalcium phosphate and cellulosic materials), disintegrating agents (e.g. starch polymers and cellulosic materials) and lubricating agents (e.g., stearates and talc). These tablets and equivalent solid and semi-solid dosage forms may be prepared by wet granulation, e.g. using an aqueous solution or an organic solution, as well as by direct compression.

Examples of progestogenic components which may suitably be used in accordance with the present invention include: levonorgestrel, norgestimate, norethisterone, dydrogesterone, drospirenone, 3-beta-hydroxydesogestrel, 3-ketodesogestrel, 17-deacetylnorgestimate, 19-norprogesterone, acetoxypregnenolone, allylestrenol, amgestone, chlormadinone, cyproterone, demegestone, desogestrel, dienogest, dihydrogesterone, dimethisterone, ethisterone, ethynodiol diacetate, fluorogestone acetate, gastrinone, gestodene, gestrinone, hydroxymethylprogesterone, hydroxyprogesterone, lynestrenol, mecirogestone, medroxyprogesterone, megestrol, mele,gestrol, nomegestrol, norethindrone, norethynodrel, norgestrel (including d-norgestrel, and dl-norgestrel), norgestrienone, normethisterone, progesterone, quingestanol, (17 alpha)-17-hydroxy-11-methylene-19-norpregna-4, 15-dien-20-yn-3-one, tibolone, trimegestone, algestone-acetophenide, nestorone, promegestone, 17-hydroxyprogesterone esters, 19-nor-17hydroxyprogesterone, 17alpha-ethynyltestosterone, 17alpha-ethynil-19-nortestosterone, d-17beta-acetoxy-13beta-ethyl-17alpha-ethynylgon-4-en-3 -one oxime, 6beta, 7beta; 15beta,16beta-dimethylene-3 -oxo-17-pregna-4,9 (11)-diene-21, 17beta-carbolactone or tanaproget and precursors of these compounds that are capable of liberating these progestogens in vivo when used in the present method.

Preferably the progestogenic component used in the present method is selected from the group consisting of progesterone, desogestrel, gestodene, dienogest, levonorgestrel, norgestimate, norethisterone, drospirenone, trimegestone, dydrogesterone, precursors of these progestogens and mixtures thereof.

When the progestogenic component of the invention is drospirenone, it is preferably used at a daily dose of from 0.5 mg to 10 mg, even more preferably of from 1 mg to 4 mg. In a most preferred embodiment, the progestogenic component of the invention is drospirenone and it is used at a daily dose of about 3 mg.

When a different progestogenic component is used, the daily dose is adjusted such as to give the same pharmacological effect as a dose of 0.5 mg to 10 mg of drospirenone, preferably to give the same pharmacological effect as a dose of 1 mg to 4 mg of drospirenone.

In a preferred embodiment of the invention, the composition combines estetrol at a daily dose of from 5 mg to 25 mg with drospirenone at a daily dose of 0.5 mg to 10 mg. In a more preferred embodiment of the invention, the composition combines estetrol at a daily dose of from 10 mg to 20 mg with drospirenone at a daily dose of 1 mg to 4 mg. In a yet more preferred embodiment of the invention, the composition combines estetrol at a daily dose of about 15 mg with drospirenone at a daily dose of about 3 mg.

In particular embodiments of the invention, the composition does not contain any added zinc salts. In these embodiments, no biocompatible zinc salts are used for the preparation of the compositions according to the invention.

The present invention has been described above with reference to a number of exemplary embodiments. Modifications and alternative implementations of some parts or elements are possible, and are included in the scope of protection as defined in the appended claims.

EXAMPLES

Example 1

During that study, healthy female subjects were treated for one 28-day cycle with either 10 or 20 mg E4 alone (n=10 and 11, respectively) or with a combination of E4 with either Progesterone (P) or Desogestrel (DSG) (n=15 or 16, respectively).

At baseline, occasional dysmenorrhea was reported by 11 subjects (21.2%), and frequent dysmenorrhea was reported by 19 subjects (36.5%). The distribution of dysmenorrhea is shown in Table 2 below. Overall, dysmenorrhea was reported by 25% to 53.3% of the subjects included in this trial.

TABLE 2

Reports at Baseline

| Dysmenorrhea | Number (%) of subjects | | | |
| --- | --- | --- | --- | --- |
| | 10 mg E4 (n = 10) | 20 mg E4 (n = 11) | 20 mg E4/DSG (n = 15) | 20 mg E4/P4 (n = 16) |
| No | 4 (40.0) | 7 (63.6) | 5 (33.3) | 6 (37.5) |
| Occasional | 2 (20.0) | 1 (9.1) | 2 (13.3) | 6 (37.5) |
| Frequent | 4 (40.0) | 3 (27.3) | 8 (53.3) | 4 (25.0) |

TABLE 2-continued

Reports at Baseline

| Dysmenorrhea | Number (%) of subjects | | | |
| --- | --- | --- | --- | --- |
| | 10 mg E4 (n = 10) | 20 mg E4 (n = 11) | 20 mg E4/DSG (n = 15) | 20 mg E4/P4 (n = 16) |
| Total number of subjects presenting dysmenorrhea at baseline | 6 (60.0) | 4 (36.4) | 10 (66.7) | 10 (62.5) |

As shown in Table 3 of Treatment-emergent adverse events (TE-AE) below, reporting of dysmenorrhea during the treatment phase was low in comparison to the incidence recorded at baseline. Interestingly, E4 alone seemed to have a positive impact on the incidence of dysmenorrhea without any dose-related proportionality.

TABLE 3

Treatment-emergent adverse events

| TE-AE | Number (%) of subjects | | | |
| --- | --- | --- | --- | --- |
| | 10 mg E4 (n = 10) | 20 mg E4 (n = 11) | 20 mg E4/DSG (n = 15) | 20 mg E4/P4 (n = 16) |
| Dysmenorrhea | 1 (10.0) | 1 (9.1) | 0 | 2 (12.5) |

Example 2

In this clinical study comparing different doses and different combinations of estrogenic components and progestogenic components according to the invention, overall, at baseline, 68.9% of subjects had previously experienced dysmenorrhea, which was occasional in 40.4% of subjects and frequent in 28.5% of subjects.

As illustrated in Table 4 below extracted from Treatment-emergent adverse events (TE-AE) reported by at least 2 subjects in any treatment group, dysmenorrhea was more rarely reported when the progestogenic component was drospirenone than when it was levonorgestrel.

Additionally, and quite surprisingly, it is also seen in Table 4 that the lowest dose of the estrogenic component (15 mg daily) leads to fewer reports of dysmenorrhea as TE-AE than the higher dose (20 mg daily).

TABLE 4

Treatment-emergent adverse events

| TE-AE | Number (%) of subjects | | | |
| --- | --- | --- | --- | --- |
| | 20 mg E4/150 µg LNG (n = 77) | 20 mg E4/3 mg DRSP (n = 75) | 15 mg E4/150 µg LNG (n = 80) | 15 mg E4/3 mg DRSP (n = 79) |
| Dysmenorrhea | 5 (6.5) | 4 (5.3) | 3 (3.8) | 2 (2.5) |

Finally, dysmenorrhea TE-AEs leading to discontinuation occurred once in each of the 20 mg E4 groups (1.3%) but did not occur in any of the 15 mg E4 groups (0%).

Example 3

In this clinical study comparing the combination of estrogenic component and progestogenic component according to the invention with a commercially available contraceptive treatment using also a natural estrogen (estradiol valerate at a 1, 2 or 3 mg dose of with dienogest at a dose of 0, 2 or 3 mg, marketed as Qlaira® by Bayer HealthCare, Germany), the number of drug-related adverse events (Treatment-emergent adverse events (TE-AE) reported by at least 2 subjects in any treatment group) and the levels of the SHBG marker were monitored.

As illustrated in Table 5 below, 13 subjects (corresponding to 16.7%) reported TE-AEs related to headache in the treatment arm with the commercial product based on estradiol valerate and dienogest, while only 6 subjects (corresponding to 7.6%) did so in the group treated with a combination of 15 mg of estetrol and 3 mg of drospirenone. The number of events related to headache was thus shown to be much lower for the treatment according to the invention.

In addition, the number of adverse events related to breast pain was similar and very low (only 1.3% of occurrences) for the two treatments.

TABLE 5

Treatment-emergent adverse events

| | Number (%) of subjects | |
|---|---|---|
| Drug-related adverse event | Qlaira E2V/DNG N = 78 | 15 mg E4/ 3 mg DRSP N = 79 |
| Headache | 13 (16.7) | 6 (7.6) |
| Breast pain | 1 (1.3) | 1 (1.3) |

In addition in this study, changes in SHBG concentrations were sequentially assessed at baseline and during Cycle 4 and Cycle 6 of administration of the combinations of E4/DRSP and E2V/DNG to women starting combined contraception (groups of patient called "Starters"). Women were defined as Starters when they had not used a hormonal contraceptive in the 3 months prior to randomisation. This "wash-out" period allowed to exclude patients whose SHBG levels were influenced by the previous COC used. The results in terms of changes rom baseline are shown in Table 6 below.

TABLE 6

Mean percentage SHBG level changes from baseline to Cycle 4 and from baseline to Cycle 6

| | Mean change from Baseline (%) | |
|---|---|---|
| SHBG level (Starters) | Qlaira E2V/DNG N = 22 | 15 mg E4/ 3 mg DRSP N = 30 |
| Cycle 4/Screening | +43.9% (+/−35.6) | +27.1% (+/−12.1) |
| Cycle 6/Screening | +54.4% (+/−15.9) | +41.7% (+/−36.5) |

As is apparent from Table 6, the method of the invention permits to minimize the SHBG level changes from baseline both at Cycle 4 and at Cycle 6, compared to a commercially available COC which also uses a natural estrogen.

Example 4

In this clinical study comparing two combination of estrogenic component and progestogenic component according to the invention with a commercially available contraceptive treatment (using ethinyl estradiol at 20 microg with drospirenone at 3 mg, marketed as Yaz® by Bayer HealthCare, Germany), several haemostasis markers as well as carrier proteins were measured and changes from baseline to end of Cycle 3 in these parameters are presented below in Table 7.

TABLE 7

Mean (SD) percentage change from baseline to end of treatment Cycle 3 for haemostasis parameters and carrier proteins, in women using a combination of E4/DRSP or EE/DRSP

| | Mean (SD) percentage change | | |
|---|---|---|---|
| Parameters | 5 mg E4/DRSP (n = 17) | 10 mg E4/DRSP (n = 19) | 20 μg EE/DRSP (n = 20) |
| Molecular markers | | | |
| D dimer | −25.9 (32.71) | −22.0 (29.70) | 35.8 (56.14) |
| Prothrombin fragment 1 + 2 | −24.1 (15.97) | −1.3 (28.63) | 63.4 (50.21) |
| Group 1 coagulation inhibition | | | |
| Antithrombin III | 1.6 (8.23) | 1.5 (11.36) | −5.2 (7.88) |
| APC resistance (Rosing) | 3.0 (26.19) | 6.6 (37.45) | 227.5 (181.27) |
| Protein S activity | 8.6 (11.78) | 5.2 (10.29) | −27.4 (10.88) |
| Free TFPI | −13.5 (15.33) | −15.1 (8.89) | 46.6 (8.50) |
| Group 2 coagulation inhibition | | | |
| Protein C activity | −3.7 (9.95) | −0.5 (10.18) | 15.8 (13.82) |
| APC sensitivity (APTT) | 0 (9.77) | −2.7 (8.88) | −9.8 (9.74) |
| Liver factors | | | |
| Fibrinogen | 5.8 (12.24) | −0.6 (15.37) | 19.5 (23.78) |
| Prothrombin | 11.7 (34.71) | 21.4 (24.98) | 13.8 (21.76) |
| Endothelial factors | | | |
| Eselectin | 3.2 (10.45) | −6.7 (14.00) | −19.5 (8.06) |
| tPA | −8.4 (25.76) | −15.7 (24.25) | −45.8 (14.05) |
| Carrier proteins | | | |
| CBG | 17.1 (16.64) | 28.1 (19.55) | 170.3 (75.60) |
| SHBG | 7.9 (26.25) | 44.5 (34.12) | 306.3 (117.70) |
| Ceruloplasmin | 8.2 (12.24) | 16.1 (11.14) | 69.0 (22.93) |

E4, estetrol; EE, ethinylestradiol; DRSP, drospirenone; APC, activated protein C; TFPI, tissue factor pathway inhibitor; tPA, tissue type plasminogen; CBG, corticosteroid binding globulin; SHBG, sex hormone binding globulin.

A large difference was observed between DRSP combinations containing 20 microg EE and those with 5 or 10 mg E4: the procoagulant marker Prothrombin Fragment 1+2 plasma levels were decreased with the different E4/DRSP combinations, whereas they increased with EE/DRSP (+63% from baseline to 3 months of use). These opposite results indicate that increase in the thrombosis marker Prothrombin Fragment 1+2 is bound to the type (and dose) of estrogens (here EE vs. E4). Moreover, natural anticoagulants were unchanged (antithrombin III, protein S activity) or slightly decreased (free TFPI) by combinations containing E4 and typically decreased by EE/DRSP. While, as usual, activated partial thromboplastin time (APTT) related sensitivity to APC was almost unchanged with all preparations, the normalized APC sensitivity ratio was unchanged with E4 combinations whereas resistance to protein C was strongly increased by the EE/DRSP combination. Simultaneously to the non-increase of the procoagulant markers when using combinations of E4 and DRSP, there was a slight decrease in fibrinolysis parameters such as tPA and D-dimers levels.

With EE/DRSP combination, the increase in SHBG was important (+306%). All combinations of E4 (5, 10 mg) with DRSP showed a moderate increase in SHBG. Note that SHBG is considered as the most relevant biomarker for estrogenic impact of a COC on liver metabolism (Odlind V. et al.; *Acta Obstet Gynecol Scand* 2002; 81:482). CBG and ceruloplasmin are essentially synthesized under the influence of estrogens and are much less sensitive to the androgenic action of progestins. In the E4 and DRSP groups, increasing the dose of estrogen resulted in a slight increase from baseline for CBG and ceruloplasmin. However, by far the largest change from baseline was observed in the EE/DRSP group compared to the E4 treatment groups.

Example 5

A multicenter, placebo-controlled, randomised study to evaluate the benefits of the method of the invention on alleviating complaints of dysmenorrhea was conducted. The study population consisted in healthy female subjects, between 12 and 35 years old, inclusive (at the time of screening), with primary dysmenorrhea (onset <3 years post menarche).

The product according to the method of the invention was a combination tablet with estetrol (15 mg) and drospirenone (3 mg) administered orally once daily in continuous or 24/4-day regimen (i.e. 24 days of active tablets followed by 4 days of placebo tablets). Other doses of estetrol were included in supplementary arms, in addition to the placebo arm.

The efficacy of the method of the invention was demonstrated by following the change between baseline evaluation period and treatment evaluation period, primarily in the number of days with dysmenorrhea pain.

Dysmenorrhea pain was defined as pelvic pain during the menstrual/withdrawal bleeding episode and the 2 days before this episode.

Secondarily, the efficacy was followed by a daily scoring of dysmenorrhea pain, according to the following scale:
0—No pain;
  1—Mild pain with no need for painkiller;
  2—Moderate pain with need for painkiller;
  3—Severe pain with need for painkiller.

Additional efficacy assessment were made as follows:
1. Change Between Baseline Evaluation Period and End of Treatment Evaluation Period in Number of Days With Pelvic Pain Independent of Occurrence of Vaginal Bleeding;
2. Change Between Baseline Evaluation Period and Treatment Evaluation Period in Number of Days With Pelvic Pain During Unscheduled Bleeding;
3. Change Between Baseline Evaluation Period and Treatment Evaluation Period in Rescue Medication Use. Rescue medication use will be standardized intake of 200 mg Ibuprofen tablets;
4. Percentage of Participants With Interference of Dysmenorrhea Pain With Work/School and Social or Other Activity;
5. Percentage of Participants and Hours/Days of Missing Time From Work Due to Dysmenorrhea Pain at Baseline, Month 3 and Final Examination (after Month 6);
6. Percentage of Participants Satisfied With Study Treatment;
7. Own Costs of Physiotherapy, Alternative Medicine, Acupuncture, Osteopathy, Medical Counselling, Massages, Herbal supplements/Teas per treatment of dysmenorrhea pain evaluated by completion of a Resource Use Questionnaire (converted to euros);
8. Patient's improvement during the course of study as per The Clinical Global Impression Scale (CGI) completed by Investigators;
9. Participants' Assessment in the Clinical Global Impression The Clinical Global Impression Scale (CGI) as completed by the participants and rating their improvement during the course of the study;
10. General Health, Body Pain, Physical and Social Functioning, Mental Health and Vitality as measured by General Health and Well-being Questionnaire SF-36 at Baseline, Month 3 and at Final Examination, using the SF-36 self-administered questionnaire, a general health status measure used to evaluate patient populations and to compare health status across different populations.

The clinical study demonstrates that the product according to the invention is effective in improving the symptoms of dysmenorrhea.

Example 6

A multi-institutional, placebo-controlled trial was conducted with collaborative randomized allocation double-blinded control for dysmenorrhea patients (primary dysmenorrhea patients, and secondary dysmenorrhea patients) aged 16 and older.

The study drug is a combination tablet containing estetrol (15 mg) and drospirenone (3 mg).

The tablet has two modes of administration:
for cyclic administration, the study drug was given orally in a cycle consisting of administration of one tablet per day at the same time every day for 24 days, followed by a 4-day discontinuation period;
for continued administration, the study drug was continuously administered, without discontinuation, in a dose of one tablet per day at the same time every day.

For primary evaluation, changes from baseline were scored at week 16 (4 cycles) according to the evaluation scale in Table 8 below.

TABLE 8

Dysmenorrhea score involving severity of dysmenorrhea as well as use of analgesics as reported in Harada T et al., Low-dose oral contraceptive pill for dysmenorrhea associated with endometriosis: a placebo-controlled, double-blind, randomized trial, Fertil Steril 2008; 90: 1583-1588

|  | Grade | Score | Details |
|---|---|---|---|
| Dysmenorrhea (or nonmenstrual pelvic pain) | None | 0 | none |
|  | Mild | 1 | some loss of work (or study) efficiency |
|  | Moderate | 2 | want to take some rest in bed, loss of work |
|  | Severe | 3 | in bed more than 1 day |
| Use of analgesics (previous or present period) | None | 0 | none |
|  | Mild | 1 | take analgesics for 1 day |
|  | Moderate | 2 | take analgesics for 2 days |
|  | Severe | 3 | take analgesics for >3 days |

Additional efficacy assessments were made as follows:
1. dysmenorrhea pain was evaluated by observing changes from baseline using a VAS scale and pelvic pain scores;
2. occurrence of abnormal vaginal bleeding was evaluated;

3. amelioration of premenstrual syndrome was evaluated by observing changes from baseline using a self-administered questionnaire;
4. potential risk of the study drug on venous thromboembolism (VTE) was evaluated using surrogate markers of VTE (e.g., D-dimer, SHBG, protein C activity, and protein S activity);
5. changes in the severity of lower abdominal pain, lower back pain, headache, vomiting, and a feeling of sickness during menstruation;
6. changes in endometrial thickness from baseline;
7. serum CA125 concentration, and serum C reactive protein concentration;
8. serum estradiol concentration, and serum progesterone concentration;
9. safety items:
   adverse events;
   clinical test results (including an endocrine test), vital signs;
   uterine size.

The clinical study demonstrates that the product according to the invention is effective in improving the symptoms of dysmenorrhea.

The invention claimed is:

1. A method for preventing pregnancy, comprising orally administering to a female subject a composition comprising from 15 to 25 mg estetrol and from 1 to 4 mg drospirenone, wherein administration of said composition does not result in a hemostatic change exceeding a boundary of a normal hemostatic range.

2. The method according to claim 1, wherein the subject has dysmenorrhea, and wherein administration of said composition results in preventing or alleviating symptoms of dysmenorrhea in the subject.

3. A method for preventing pregnancy, comprising orally administering to a female subject a composition comprising from 15 to 25 mg estetrol and from 1 to 4 mg drospirenone, wherein administration of said composition does not result in an increased risk of developing venous thromboembolism (VTE) in the subject.

4. A method for preventing pregnancy, comprising orally administering to a female subject a composition comprising from 15 to 25 mg estetrol and from 1 to 4 mg drospirenone, wherein the subject's risk of developing VTE associated with administration of said composition is lower as compared to the risk associated with administration of other combined oral contraceptives.

5. The method according to claim 1, wherein no hemostatic change that exceeds the boundaries of the normal hemostatic range occurs upon administration of the composition.

6. The method according to claim 1, wherein the normal hemostatic range is defined as a prediction interval that 95% of the target patient population falls into.

7. The method according to claim 1, wherein said hemostatic change is determined based on a change in any one or more of the following markers: SHBG, free TFPI, free and total Protein-S, Protein-S activity, CBG, Ceruloplasmin, antithrombin III, APC resistance, protein-C activity, D-dimer, Prothrombin, Prothrombin fragment 1+2, Factor VII, Factor VIII, von Willebrand factor, Factor II, PAI-I, t-PA, plasminogen, E-selectin, and fibrinogen.

8. The method according to claim 1, wherein said hemostatic change is determined based on a change in level of Protein-S or TFPI.

9. The method according to claim 1, wherein said hemostatic change is measured after one cycle of treatment, after two cycles of treatment or after three cycles of treatment.

10. The method according to claim 1, wherein the composition comprises from 15 to 20 mg estetrol.

11. The method according to claim 1, wherein the composition comprises about 15 mg estetrol.

12. The method according to claim 1, wherein the composition comprises about 20 mg estetrol.

13. The method according to claim 1, wherein the composition comprises about 3 mg drospirenone.

14. The method according to claim 1, wherein said estetrol is estetrol monohydrate.

15. The method according to claim 1, wherein said composition comprises about 15 mg of estetrol and about 3 mg of drospirenone.

16. The method according to claim 1, wherein said composition is administered for 21 to 24 days, followed by an administration-free period of about 7 to 4 days.

17. A method of contraception that avoids hemostatic changes exceeding a boundary of a normal hemostatic range in a subject, comprising administering to the subject a combined oral contraceptive (COC) comprising from 15 to 25 mg estetrol and from 1 to 4 mg drospirenone.

18. The method according to claim 17, wherein the subject has dysmenorrhea, and wherein administration of said COC results in preventing or alleviating symptoms of dysmenorrhea in the subject.

19. A method of contraception that avoids hemostatic changes exceeding a boundary of a normal hemostatic range in a subject, comprising administering to the subject a combined oral contraceptive (COC) comprising from 15 to 25 mg estetrol and from 1 to 4 mg drospirenone, wherein administration of said COC does not increase the subject's risk of developing VTE.

20. The method according to claim 17, wherein said composition comprises about 15 mg of estetrol and about 3 mg of drospirenone.

* * * * *